(12) United States Patent
Maruo

(10) Patent No.: US 7,307,261 B2
(45) Date of Patent: Dec. 11, 2007

(54) FLUORESCENCE DETECTING APPARATUS

(75) Inventor: Yuji Maruo, Hachiouji (JP)

(73) Assignee: Sharp Kabushiki Kaisha, Osaka (JP)

( * ) Notice: Subject to any disclaimer, the term of this patent is extended or adjusted under 35 U.S.C. 154(b) by 0 days.

(21) Appl. No.: 11/397,893

(22) Filed: Apr. 5, 2006

(65) Prior Publication Data

US 2006/0226375 A1 Oct. 12, 2006

(30) Foreign Application Priority Data

Apr. 6, 2005 (JP) .............................. 2005-109906

(51) Int. Cl.
*G01N 21/64* (2006.01)
(52) U.S. Cl. .................................. 250/458.1
(58) Field of Classification Search ............ 250/458.1
See application file for complete search history.

(56) References Cited

U.S. PATENT DOCUMENTS 6,545,758 B1 * 4/2003 Sandstrom ................... 356/317
2003/0230728 A1 * 12/2003 Dai et al. ................ 250/458.1

FOREIGN PATENT DOCUMENTS

JP 9-210907 A 8/1997
JP 2004-279258 A 10/2004

OTHER PUBLICATIONS

Unuma, "Development of High-Speed Full-Automatic Portable Two-Dimensional Electrophoresis Device", Reprint, No. 67th Symposium of Analytical Chemistry, May 13-14, 2006 and partial English translation thereof.

* cited by examiner

*Primary Examiner*—David Porta
*Assistant Examiner*—Mark R. Gaworecki
(74) *Attorney, Agent, or Firm*—Nixon & Vanderhye, P.C.

(57) ABSTRACT

A fluorescence detecting apparatus includes: a light source for illuminating the surface of detection of a sample with excitation light; a CCD area image sensor for detecting fluorescence emitted from the sample; and a micromirror array device for irradiating excitation light in a 2-dimensional illumination pattern generated by an information processor based on the detected result from the CCD area image sensor. In this configuration, irradiation of weak excitation light on areas that contain large amounts of fluorescent dyes hence would emit strong fluorescence makes it possible to excite reduced amounts of fluorescence and thereby inhibit adverse effects such as blurring or spreading of light of fluorescent wavelengths around the areas as well as to prevent the high-sensitivity fluorescence detecting device from being saturated by excessive amounts of light. On the other hand, irradiation of strong excitation light on areas that contain lower amounts of fluorescent dyes hence would emit weak fluorescence makes it possible to obtain high enough amounts of fluorescence that can be detected by the fluorescence detecting device.

9 Claims, 6 Drawing Sheets

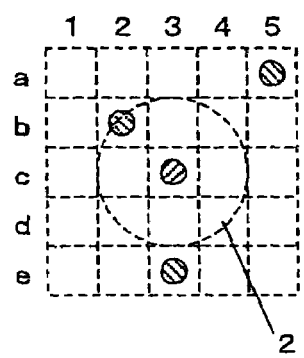

It is possible to detect both spots of fluorescence by illuminating area 4 with strong excitation light while illuminating area 5 with weak excitation light.

It is difficult to detect weak fluorescence because of increase in background level in area 3 due to emission of strong fluorescence.

FLUORESCENCE DETECTING APPARATUS

This Nonprovisional application claims priority under 35 U.S.C. § 119(a) on Patent Application No. 2005-109906 filed in Japan on 6 Apr. 2005, the entire contents of which are hereby incorporated by reference.

BACKGROUND (1) Technical Field

The present invention relates to a light detecting apparatus for detecting light intensity of fluorescence, reflected light, transmitted light, etc., obtained by illuminating an object under observation with light, and mainly relates to an apparatus which detects fluorescence distribution when excitation light is irradiated, in particular, relating to a fluorescence detecting apparatus for detecting 2-dimensional separation and development of a fluorescence-labeled sample by electrophoresis etc.

(2) Related Art and Other Considerations

Generally, methods for obtaining information of an object to be observed by an optical detecting means that illuminates an object under observation with light have been used since a long time ago, for various purposes in various technical fields. Also there have been developed and used various kinds of light detecting devices which collect fluorescence, reflected light etc., emitted from an object under observation by illumination of light, onto a photo-electric transducer and detect light intensity as electric signals to thereby obtain information on the object under observation.

In detection of light intensity, detection accuracy can be improved by use of optical means such as light-separating devices, optical filters etc., that remove components of wavelengths and/or polarized light unnecessary for detection, from the light emitted from an object of study when the object is illuminated.

In particular, when the object under observation is a fluorescent material, it is possible to detect weak fluorescence because, in general, the fluorescence to be detected is different in wavelength from the excitation light for illumination. Though not particularly limited to the field of fluorescence detection, as one example of conventional light detection apparatuses, there are fluorescence detecting apparatuses that detect fluorescence distribution when excitation light is irradiated. Of these, some of fluorescence detecting apparatuses that detect 2-dimensional separation and development of a fluorescence-labeled sample by electrophoresis etc., are demanded to have detection performance with high sensitivity over a wide dynamic range in order to deal with detection from an extremely small amount of fluorescent dyes to a certain amount of fluorescent dyes.

As the conventional fluorescence detecting apparatuses, two kinds of apparatuses have been mainly used, namely, scan-type fluorescence detecting apparatus and camera-type fluorescence detecting apparatus. With regard to the scan-type fluorescence detecting apparatus, a laser beam of excitation light is irradiated to the detection point so that the fluorescence from the irradiated point is detected by a PMT (photomultiplier tube), and this irradiation and detection is scanned throughout the object to be observed to thereby obtain fluorescence information of a 2-dimensional area (Japanese Patent Application Laid-open H09-210907).

On the other hand, with regard to the camera-type fluorescence detecting apparatus, excitation light is irradiated on the area to be detected by an area light source so that fluorescence from a wide area is captured all at once by a CCD (charge coupled devices) area image sensor to thereby obtain fluorescence information of a 2-dimensional region. In most cases, CCD is cooled to reduce dark current noise and achieve high sensitivity.

For example, the sample fractionated in a 2-dimensional region by 2-dimensional electrophoresis using a gel plate etc., is processed through a dyeing step using fluorescent dyes before or after electrophoresis, and is detected as a distribution of fluorescence spots by the fluorescence detecting apparatus.

FIG. 1 is a view showing a conventional camera-type fluorescence detecting apparatus.

Light from a lamp source 90 passes through an optical filter 91 which transmits selected wavelengths for excitation light, a lens 92 or the like for condensing light on a predetermined position, to be irradiated on a sample surface 93. A fluorescently labeled sample emits fluorescence as it is irradiated with excitation light, and the fluorescence passes through an optical filter 94 which transmits the fluorescence wavelengths only and a lens 95 or the like for focusing light on and around the sample surface, and enters a CCD area image sensor 96. Since the distribution information of the fluorescent spots of the sample is obtained as an image as a whole by CCD area image sensor 96, it is possible to perform detection over the 2-dimensional area in a relatively short period.

In a 2-dimensional separation and observation of proteins or the like, capability of separation and detection of an extremely trace amount of sample is demanded. In order to obtain a more amount of information from 2-dimensional separation, it is considered that not only conventional static observation after separation but also a dynamic area-observation for detecting the continuous separation process by electrophoresis or the like is needed.

However, in the aforementioned conventional fluorescence detecting apparatus configurations, it has been impossible for any of the apparatus configurations to accomplish both the purpose of detecting separation of an extremely trace amount of a sample and the purpose of detecting a continuous separation process of the sample at the same time.

Since in the scan-type fluorescence detecting apparatus spot detection is performed using irradiation of a laser beam of excitation light, this configuration has extremely little adverse effect from light other than the irradiated point, hence is excellent in detection sensitivity. However, it takes long time for detection because detection is performed basically one spot at a time and scanning needs to be performed over the entire 2-dimensional area. Accordingly, it is practically impossible to perform a continuous process of separation except when separation and change of the sample is very slow.

In contrast, in the camera-type fluorescence detecting apparatus, it is possible to detect the fluorescence information of the image-taken area as a whole at almost the same time since the 2-dimensional area is shot at once, and hence it is possible to detect a continuous process of separation by taking images every predetermined period. However, since in this configuration the image pickup area is illuminated as a whole by an area light source, it is impossible to detect and separate weak fluorescence if there are a multiple number of fluorescent spots in the area under observation because light of fluorescence wavelengths spreads over the whole area hence increases background intensity. Further, this tendency becomes more serious in the area proximity to a bright spot that emits strong fluorescence, hence weak fluorescent spots become hard to separate, getting buried.

In conclusion, 2-dimensional separation and observation suffers the problem in that it was practically impossible for the conventional fluorescence detecting apparatus configurations to perform continuous detection of fluorescence in the process in which faint fluorescent spots from an extremely trace amount of sample become fractionated.

BRIEF SUMMARY

The present invention has been devised to solve the above conventional problems, it is therefore an object of the present invention to provide a fluorescence detecting apparatus which enables separation and detection of weak fluorescent spots emitted from an extremely trace amount of sample, in a 2-dimensional area and enables detection of the continuous changes of a process.

In order to achieve the above object, the fluorescence detecting apparatus according to an example embodiment is configured and characterized as follows:

A fluorescence detecting apparatus comprises: a light source device for illuminating a sample with excitation light; a fluorescence detecting device for detecting fluorescence emitted from the sample; and an excitation light pattern generating device for generating an illumination pattern of excitation light to be irradiated over the surface under observation of the sample, in accordance with the detected result from fluorescence detecting device.

The fluorescence detecting apparatus is further characterized in that the excitation light pattern generating device comprises a micromirror array device.

Also the fluorescence detecting apparatus is characterized in that the excitation light pattern generating device comprises a reflection-type liquid crystal device.

Furthermore, the fluorescence detecting apparatus is characterized in that the excitation light pattern generating device comprises a transmission-type liquid crystal device.

Moreover, the fluorescence detecting apparatus is characterized in that the fluorescence detecting device comprises a CCD area image sensor.

Still more, the fluorescence detecting apparatus is characterized in that the fluorescence detecting device comprises an electronic cooling device.

Finally, the fluorescence detecting apparatus is characterized in that the excitation light pattern generating device is arranged so that the minimum unit area of the excitation light pattern generating device which receives excitation light irradiated from the light source device and generates a pattern of the excitation light and the unit detection area of the fluorescence detecting device are approximately equal in size and position to each other on the sample surface from which fluorescence is emitted.

With the above configuration, it is possible to irradiate different intensities of excitation light optimal for individual places on the sample surface at almost the same time. That is, irradiation of weak excitation light on areas that contain large amounts of fluorescent dyes hence would emit strong fluorescence makes it possible to excite reduced amounts of fluorescence and thereby inhibit adverse effects such as blurring or spreading of light of fluorescent wavelengths around the areas as well as to prevent the high-sensitivity fluorescence detecting device from being saturated by excessive amounts of light. On the other hand, irradiation of strong excitation light on areas that contain lower amounts of fluorescent dyes hence would emit weak fluorescence makes it possible to obtain high enough amounts of fluorescence that can be detected by the fluorescence detecting device.

As described above, the apparatus includes: a light source device for illuminating a sample with excitation light; a fluorescence detector for detecting fluorescence emitted from the sample; and an excitation light pattern generator disposed in the light path from the light source to the sample for generating a 2-dimensional illumination pattern of excitation light to be irradiated over the sample surface in accordance with the detected result from the fluorescence detector. It is therefore possible to irradiate different intensities of excitation light optimal for individual places on the sample surface at almost the same time.

Further, by illuminating areas that contain large amounts of fluorescent dyes hence would emit strong fluorescence, with weak excitation light it is possible to emit reduced amounts of fluorescence and thereby inhibit adverse effects such as blurring or spreading of light of fluorescent wavelengths around the areas as well as to prevent the high-sensitivity fluorescence detecting device from being saturated by excessive amounts of light. On the other hand, by illuminating areas that contain lower amounts of fluorescent dyes hence would emit weak fluorescence, with strong excitation light it is possible to obtain high enough amounts of fluorescence that can be detected by the fluorescence detecting device.

BRIEF DESCRIPTION OF THE DRAWINGS

FIG. 3 is a chart of partial images for illustrating the operation of a fluorescence detecting apparatus according to the first example embodiment;

DETAILED DESCRIPTION

The embodiment of the present invention will hereinafter be described with reference to the accompanying drawings.

<Description of the First Embodiment>

Figure 1:
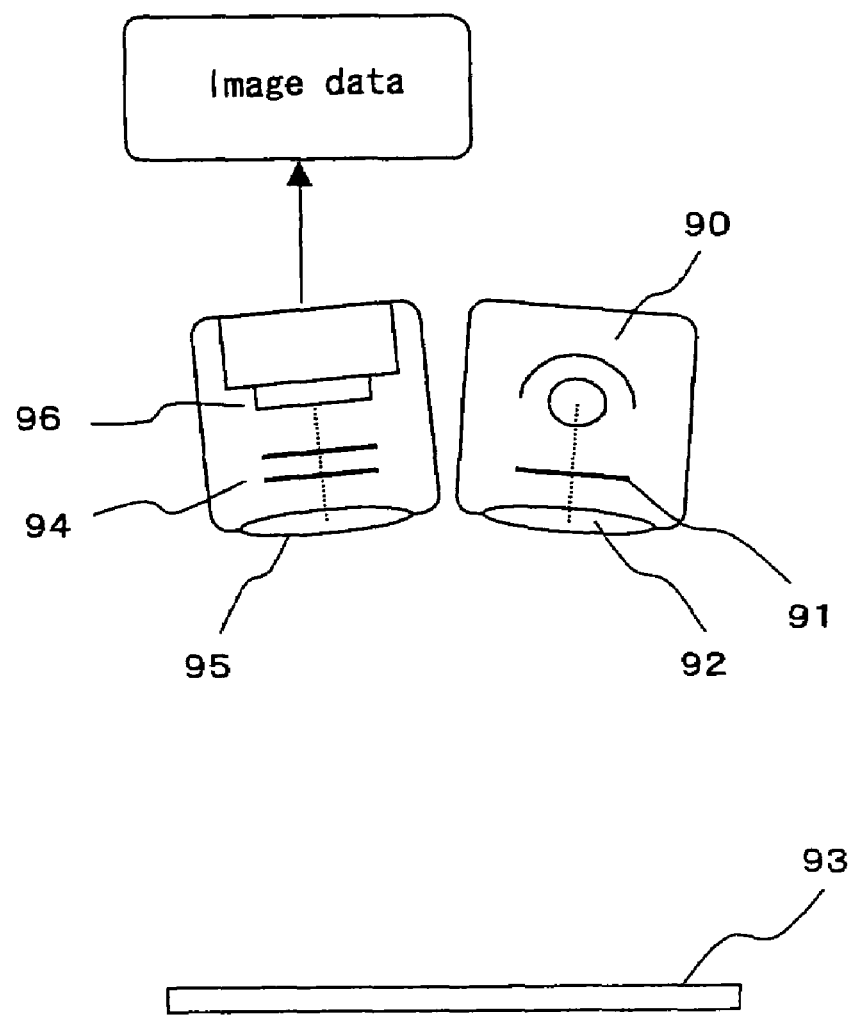
FIG. 1 is a sectional view showing a schematic configuration of a conventional fluorescence detecting apparatus.
Figure 2:
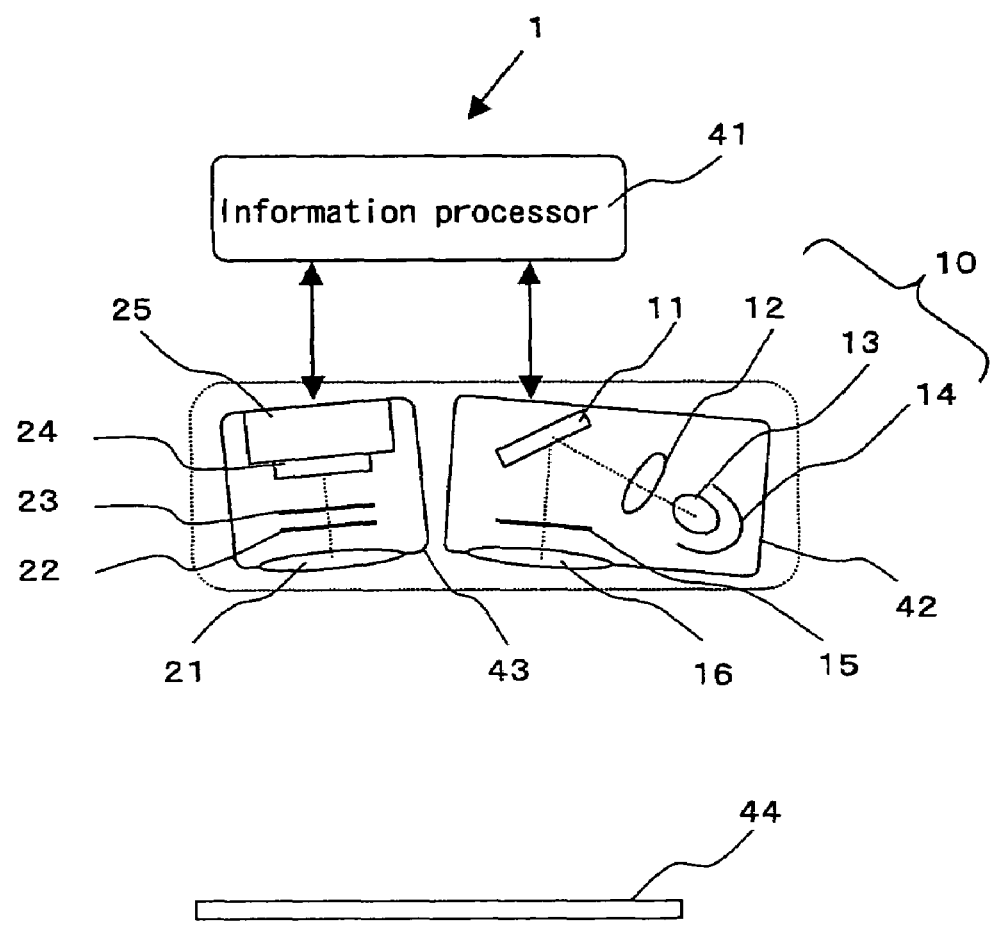
FIG. 2 is a sectional view showing a schematic configuration of a fluorescence detecting apparatus according to the first example embodiment.

FIG. 2 is a schematic configurational view showing the first example embodiment of a fluorescence detecting apparatus.

In this drawing, a fluorescence detecting apparatus 1 is comprised of an excitation light pattern generating illuminator 42, a fluorescence image detector 43 and an information processor 41.

In excitation light pattern generating illuminator 42, light from a light source 10 is irradiated on a micromirror array device 11, the light reflected off micromirror array device 11 passing through a projection lens 16 to be projected on a surface of detection 44 of a sample. Micromirror array device 11 is composed of a plurality of angle-variable micro mirrors as many number as the pixels of the projection image pattern, and the angle switching actions of individual micromirrors can be controlled by PWM (pulse width modulation) control to determine grayscales.

Light source 10 is composed of a light source mirror 14 arranged at the rear of lamp 13 and a light source lens 12 for irradiating light onto micromirror array device 11.

Micromirror array device 11 is PWM controlled by a control circuit in accordance with the excitation light pattern generating information, described hereinbelow, so that the directions of reflection of light from light source 10 are controlled by individual micromirrors, to thereby form a 2-dimensional excitation light pattern on the surface of detection 44 of the sample.

When lamp 13 of light source 10 is a white-light source or the like, emitting light over a wide range of wavelengths, an optical filter 15 such as a band-pass filter, color filter, etc., is arranged in the course of the optical path in order to limit the excitation light to be illuminated on the sample within a predetermined wavelength range.

Optical filter 15 can be disposed before or behind optical lens 12, or before or behind projection lens 16. Lamp 13 of light source 10 may use a lamp such as a high-pressure mercury lamp, metal halide lamp, xenon lamp or the like, or may use a high-brightness LED, high-brightness fluorescent tube etc. Further, the configurations and shapes of light source mirror 14 and light source lens 12 or whether they should be used or not can be made choice of, considering the characteristics of light source devices such as luminescence anisotropy etc.

For micromirror array device 11, for example DMD (Digital Micro-mirror Device), a product of Texas Instrument Incorporated, can be used. Further, components of DLP (Digital Light Processing) system, a projection type projector system using that DMD may be used to configure excitation light pattern generating illuminator 42.

In fluorescence image detector 43, the fluorescence image of a sample on the surface of detection 44 is focused on a CCD (Charge Coupled Devices) area image sensor 24 by an image taking lens 21. An optical filter 22 such as a band-pass filter, notch filter, etc., is arranged in the course of the optical path in order to block light of excitation light wavelengths incident on CCD area image sensor 24 and selectively allow light of fluorescent wavelengths incident thereon for detection.

Optical filter 22 may be arranged before or behind lens 21. It is also possible to layout in the course of the optical path a shutter 23 for blocking the light path in order to control the incident timing of light onto CCD area image sensor 24.

This CCD area image sensor 24 is cooled using a cooling unit 25 made up of a thermoelectric transducer such as a Peltier device etc., to reduce dark current noise and thereby enhance its sensitivity. To achieve a further high sensitive detection, a CCD area image sensor 24 having an electron multiplying function may be used.

When component parts are so selected that the projection pixels as the minimum units of the projection pattern of excitation light pattern generating illuminator 42 and the imaging pixels as the minimum units of CCD area image sensor 24 will be made one-to-one correspondent to each other on the surface of detection 44 of a sample, both with respect to the pitch and positional relationship, this makes it possible to make the maximum use of the resolutions of both components, which is the most preferable configuration.

Pickup image information output from CCD area image sensor 24 is transferred to information processor 41 including a computer etc., byway of a control circuit (not illustrated) for driving CCD area image sensor 24, data acquisition, etc.

Information processor 41 records numerical information of the 2-dimensional area for the surface of detection 44 of a sample, including pickup image information collected by fluorescence image detector 43, excitation light pattern generating information set up by performing operations based on the pickup image information etc., fluorescence information of the sample, calculated based on the excitation light pattern generating information, the pickup image information corresponding to it and the like, and processes fluorescence detection of the sample and the like, based on the numerical information, and also controls individual components.

The hardware configuration of information processor 41 may be given as a general-purpose computer, a board computer, or an entity that is accessed through a network.

Next, the operation of fluorescence detection of fluorescence detecting apparatus 1 according to the first embodiment will be described.

FIG. 3 is a chart of partial images for illustrating the operation of fluorescence detecting apparatus 1 according to the present embodiment.

For simplicity, description is particularly simplified referring to partially extracted model areas of 5×5 pixels.

FIG. 3A is a chart showing fluorescence spots on the surface of detection.

In the drawing, fluorescence spots on the surface of detection 44 are denoted with hatched circles. A coordinate point [3, c] represents a strong fluorescence spot, coordinate points [2, b], [3, e] and [5, e] represent weak fluorescent spots.

A broken-line circle 2 designates a spreading of fluorescence of the fluorescent spot at coordinate point [3, c] when strong excitation light is irradiated.

FIG. 3B is a chart showing a fluorescence detection image when strong excitation light is irradiated.

FIG. 3C is a chart showing a fluorescence detection image when weak excitation light is irradiated.

FIG. 3D is a chart showing a fluorescence detection image when strong excitation light is irradiated on the area other than coordinate point [3, c].

FIG. 3E is a chart showing a fluorescence detection information that is obtained through the information processor by the fluorescence detecting apparatus of the present embodiment.

Upon fluorescence detection, the presumed subject to be studied by fluorescence detection is a process in which multiple fluorescent spots having markedly great differences in fluorescent intensity gradually vary in their intensity and position over time, as in a case where a previously fluorescence-labeled sample held in a gel plate or the like becomes fractionated over a 2-dimensional region by 2-dimensional electrophoresis.

To begin with, at the first step, while excitation light pattern generating illuminator 42 irradiates the whole detection area with excitation light of uniform intensity, fluorescence image detector 43 captures the fluorescence image at that time, so that information processor 41 recognizes fluorescence intensity at individual positions. Since this step is aimed at detecting fluorescent spots having intensity higher than a certain level, the intensity of excitation light illumination from excitation light pattern generating illuminator 42 is set at a weak level. Further, the imaging exposure time of area image sensor 24 by fluorescence image detector 43 may be set at a short period, or the aperture of the imaging lens optical system may be set at a high value.

In this way, the above step is able to provide a fluorescence detected image, as shown in FIG. 3C, by irradiating with weak excitation light, strong fluorescent spots on the surface of detection 44. Specifically, in this case only the strong fluorescent spot located at a coordinate point of [3, c] can be obtained.

Next, in the second step, information processor 41 generates an excitation light pattern generating information such as not to illuminate with excitation light the point and therearound in which a fluorescent spot has been detected at the previous step, and excitation light pattern generating illuminator 42 illuminates with the patterned excitation light. Since this step is aimed at detecting fluorescent spots that were hard to detect at the previous step because of their low intensity, a fluorescence image is taken by fluorescence image detector 43 while excitation light having a higher intensity than the previous step is being illuminated, and the fluorescence intensity at each position is recognized by information processor 41. Further, the imaging exposure time of area image sensor 24 by fluorescence image detector 43 may be set longer than that in the previous step, or the aperture of the imaging lens optical system may be set at a value lower than that of the previous step.

This step is able to provide a fluorescence detected image, as shown in FIG. 3D, by irradiating weak fluorescent spots on the surface of detection in FIG. 3A, in the area other than the spot at coordinates [3, c] where a strong fluorescent spot was observed, with strong excitation light.

Further, at the third step, information processor 41 provides a fluorescence-detected image of information in which individual fluorescent spots are separated from one another as shown in FIG. 3E, based on the fluorescence-detected images of information obtained at the above first and second steps. Thus, it is possible by this step to obtain fluorescence-detected image information of separated spots even when strong and weak fluorescent spots are mixed together.

Figure 4B:
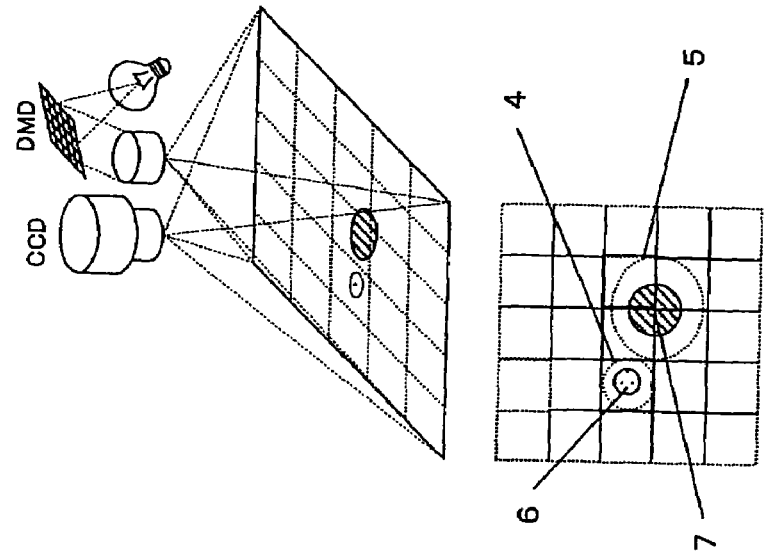
FIG. 4 is an illustration for supplementary explaining the operation of fluorescence detection of the conventional fluorescence detecting apparatus and that of a fluorescence detecting apparatus according to the present example embodiment.

Referring next to FIG. 4, the fluorescence detecting operation of the conventional fluorescence detecting apparatus and that of the fluorescence detecting apparatus 1 according to the present embodiment will be described supplementally.

FIG. 4 is an illustration for supplementally explaining the fluorescence-detecting operation of the conventional fluorescence detecting apparatus and that of the fluorescence detecting apparatus 1 of the present embodiment.

Figure 4A:
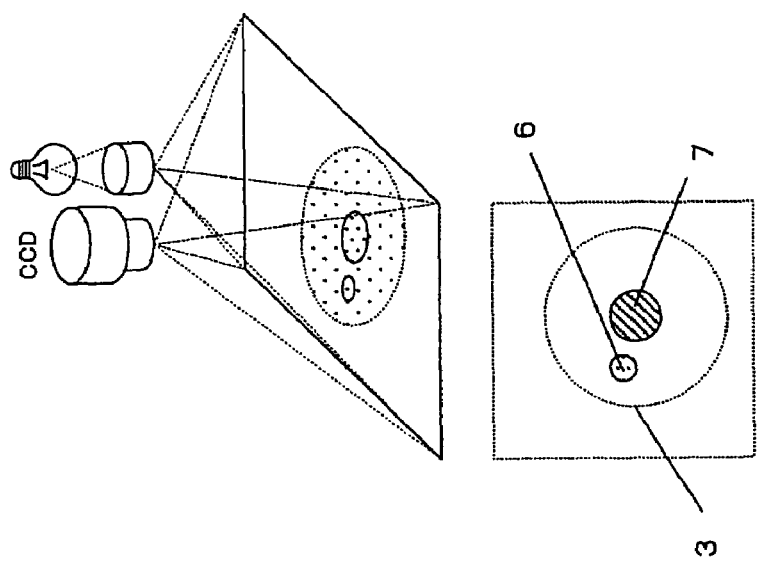

In the conventional fluorescence detecting apparatus shown in FIG. 4A, it is necessary to emit strong uniform excitation light in order to detect fluorescence from a weak fluorescent spot 6, but because of influence of the spreading of fluorescence from a strong fluorescent spot 7 when strong excitation light is illuminated, the brightness in a background area 3 (the area enclosed by a broken-line circle 2 in FIG. 3A) increases, so that it is difficult to detect weak fluorescent spots. Specifically, the fluorescence-detected image results in the one shown in FIG. 3B in which individual fluorescent spots are joined. It is hence impossible to separate fluorescent spots having different fluorescence brightness, hence difficult to achieve detection of fluorescence brightness.

In contrast, in the fluorescence detecting operation of fluorescence detecting apparatus 1 according to the present embodiment, it is possible as stated above to separate the areas by use of DMD and illuminate different areas with excitation light of different intensities. It is therefore possible to separate fluorescent spots having different fluorescence brightness from one another as shown in FIGS. 3C and 3D and detect fluorescence intensity (by separating areas into a surrounding area 4 of weak fluorescent spot 6 and a surrounding area 5 of strong fluorescent spot 7).

In fluorescence detecting apparatus 1 of the present embodiment, it is possible to implement multiple steps similar to the second step, one to another, including the N steps (N=3, 4, . . . ), aiming at executing multiple classes of the second step, whereby it becomes possible to realize an operation of a fluorescence detecting apparatus having a high sensitivity over a wide dynamic range, by effectively making use of the features of apparatus components, such as the selectable range of excitation light intensity, the sensitive range of the CCD area image sensor, the selectable range of imaging exposure time, etc. The excitation light illumination intensity, the imaging exposure time of the area image sensor and the like at the first step, as well as the excitation light illumination intensity pattern, the imaging exposure time of the area image sensor and the like at and after the second step, may be set up taking into account the characteristics of the fluorescence intensity etc. of the subject to be detected and the optical component configuration of the fluorescence image detector and the sensitivity characteristics of the CCD area image sensor etc.

Information processor 41 basically calculates the effective fluorescence intensity at every detected point on the surface of detection of the sample, based on the intensity of the irradiated excitation light and the fluorescence intensity detected correspondingly. The fluorescence intensity may be comprehensively calculated from multiple times of detection results under different detecting conditions. Further, when, for example some area at which an extremely high fluorescence is emitted is located adjacent to a detected point, in other words, when the surrounding condition exerts some influence on the detection result of the detected spot, a correction may be made taking into account the degree of that influence.

When, due to variation in the characteristics of a component such as micromirror array device 11 or the like of excitation light pattern generating illuminator 42, some irregular distribution of the intensity excitation light occurs over the surface of detection of the sample despite that the intensity of the excitation light is set uniform, when some fluctuation that is different from the designated setup occurs on the surface of detection 44 of the sample despite that a predetermined projection pattern is selected, or in any other cases, it is possible to keep the necessary uniformity by correcting the light intensity every projection pixel, which is the minimum unit of the projection pattern of excitation light pattern generating illuminator 42.

The above correction is preferably made to the excitation light pattern generating information at information processor 41 so as to correct the illumination intensity of the actual excitation light to be irradiated. Alternatively, it is also possible to make correction numerically upon the fluorescence intensity calculation at the information processor after actual detection has been made. When variation due to a component such as the CCD area image sensor or the like of fluorescence image detector 43 affects the detection result, it is also possible to make correction numerically upon fluorescence intensity calculation at information processor 41.

When the projection pixels as the minimum units of the projection pattern in excitation light pattern generating illuminator 42 and the imaging pixels as the minimum unit of imaging of the CCD area image sensor are made exactly in alignment with each other on the surface of detection 44 of a sample without any deviation in a one-to-one correspondent manner with respect to their pitch and positional relationship, it is most preferable to make the best use of both the resolutions.

However, it is not so easy to exactly match these conditions especially when devices such as the micromirror array device, CCD area image sensor etc., need to be selected from the existing devices to construct the apparatus, taking into account their cost, performances, etc.

In the fluorescence detecting apparatus 1 of the present embodiment, where the optical system is constructed so that the optical axis of excitation light pattern generating illuminator 42 to the surface of detection 44 of a sample and the optical axis of fluorescence image detector 43 are not coaxial, the correspondence between the projection pixels of the excitation light pattern generating illuminator and the imaging pixels of fluorescence image detector 43 cannot hold any more and will change if the distance to the surface of detection of a sample greatly changes. The correspondence relationship between the projection pixels of excitation light pattern generating illuminator 42 and the imaging pixels of fluorescence image detector 43, which is depends on various factors such as a discrepancy caused by the specifications of these devices, discrepancy due to variations etc., in manufacturing the apparatus, discrepancy caused by the apparatus configuration, the shape of the object to be detected and the positional relationship between these, may and should be recorded as previous information in the information processor and used to make correction.

Shown in the present embodiment is detection of fluorescence information of 2-dimensional area using 2-dimensional imaging device 24 and 2-dimensional excitation light pattern generating illuminator 42, but the present invention should not be limited to this. Similarly to the above means, detection of linear photo-sensing device such as a CCD line image sensor etc., and a linear excitation light pattern generating illuminator 42 may be used in combination so as to detect linear fluorescence information.

Further, addition of a synchronized scan mechanism makes it possible to detect fluorescence information of 2-dimensional area; only one of excitation light pattern generating illuminator 42 and fluorescence image detector 43 is given as a linear device and can be used in combination with a scan mechanism. However, a scan-wise detecting operation of 2-dimensional area needs a certain period of time, so it is not suitable for continuous detection in a short cycle time. Choice of a configuration can be made taking into account the needed cycle of dynamic observation, detection performance, manufacturing cost of the apparatus and other factors.

Further, the present embodiment has been described referring to an example using micromirror array device 11 as an excitation light pattern means, but the excitation light pattern means may employ a reflection-type liquid crystal device.

That is, it is possible to configure an excitation light pattern generating illuminator using constituents of an LCD projector using a reflection-type liquid crystal panel LCOS (liquid crystal on silicon). Other basic configuration and operation conform to the first embodiment, hence detailed description is omitted. The device used for the excitation light pattern means may and should be selected taking into consideration the excitation light wavelength range, device specifications, optical characteristics, cost and other factors.

<Description of the Second Embodiment>

Figure 5:
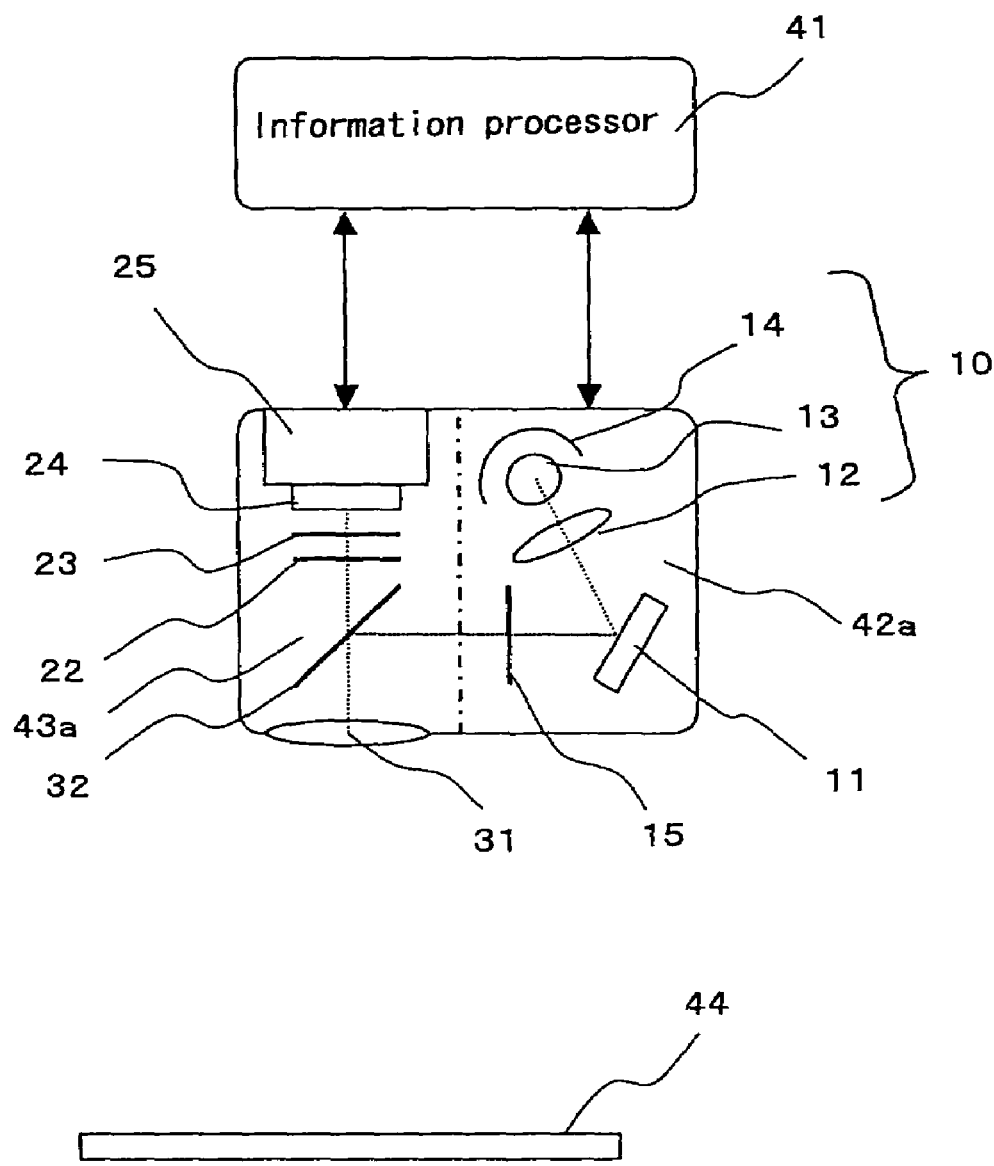
FIG. 5 is a sectional view showing a schematic configuration of a fluorescence detecting apparatus according to the second example embodiment.

FIG. 5 is a schematic configurational view showing a fluorescence detecting apparatus according to the second example embodiment.

The fluorescence detecting apparatus of the second embodiment is comprised of an excitation light pattern generating illuminator 42a and a fluorescence image detector 43a, which are arranged so as to partly share a coaxial optical system, and an information processor 41.

In excitation light pattern generating illuminator 42a, light from a light source 10 is irradiated on a micromirror array device 11, the light is further reflected off micromirrors is reflected on a dichroic mirror 32, then passes through a main lens 31 to be projected on the surface of detection 44 of a sample. Micromirror array device 11 is composed of a plurality of angle-variable micro mirrors as many number as the pixels of the projection image pattern, and the angle switching actions of individual micromirrors can be controlled by PWM (pulse width modulation) control to determine grayscales.

Light source 10 is composed of a lamp 13, a light source mirror 14 arranged at the rear of lamp 13 and a light source lens 12 for irradiating light onto micromirror array device 11.

Micromirror array device 11 is PWM controlled by the aforementioned control circuit in accordance with the excitation light pattern generating information, described hereinbelow, so that the directions of reflection of light from light source 10 are controlled by individual micromirrors, to thereby form a 2-dimensional excitation light pattern on the surface of detection 44 of the sample.

Lamp 13 of the light source is a white-light source or the like, emitting light over a wide range of wavelengths, it is necessary to limit the excitation light to be illuminated on the surface of detection 44 of the sample to a predetermined wavelength range. Because dichroic mirror 32 has a property that reflects light of a specific wavelength range and transmits light of wavelengths other than that range, the wavelength characteristics of dichroic mirror 32 can be designated in conformity with the desired wavelengths of excitation light. Further, in order to limit the wavelengths of excitation light to be illuminated on the surface of detection 44 of the sample, an optical filter 15 such as a band-pass filter, color filter, etc., can be added in the course of the optical path. Optical filter 15 can be disposed before or behind optical lens 12, or before dichroic mirror 32. Lamp 13 of light source 10 may use a lamp such as a high-pressure mercury lamp, metal halide lamp, xenon lamp or the like, or may use a high-brightness LED, high-brightness fluorescent tube etc. Further, the configurations and shapes of light source mirror 14 and light source lens 12 or whether they should be used or not can be made choice of, considering luminescence anisotropy etc.

For micromirror array device 11, DMD (Digital Micromirror Device), a product of Texas Instrument Incorporated, can be used as already mentioned above. Further, components of DLP (Digital Light Processing) system, a projection type projector system using that DMD may be used to configure excitation light pattern generating illuminator 42a.

In fluorescence image detector 43a, the fluorescence image of a sample on the surface of detection 44 is focused on a CCD (Charge Coupled Devices) area image sensor 24 by main lens 31 and dichroic mirror 32.

Because dichroic mirror 32 has a property that reflects light of a specific wavelength range and transmits light of wavelengths other than that range, the wavelength characteristics of dichroic mirror 32 is selected so as to permits fluorescence wavelengths to transmit therethrough.

In sum, the wavelength characteristics of dichroic mirror 32 is so set up as to reflect excitation light wavelengths and transmit fluorescence wavelengths.

Further, in order to block light of unnecessary wavelengths from entering CCD area image sensor 24 and selectively permit light of fluorescence wavelengths to enter thereon for detection, it is possible to add an optical filter 22 such as a band-pass filter, notch filter, etc., in the course of the optical path. In this case, optical filter 22 can be arranged behind dichroic mirror 32.

It is also possible to lay out in the course of the optical path a shutter 23 for blocking the light path in order to control the incident timing of light onto CCD area image sensor 24. This CCD area image sensor 24 is cooled using with a cooling unit 25 made up of a thermoelectric transducer such as a Peltier device etc., to reduce dark current noise and thereby enhance its sensitivity. To achieve a further high sensitive detection, a CCD area image sensor 24 having an electron multiplying function may be used.

If component parts are so selected that the projection pixels on the surface of detection 44 of a sample, as the minimum units of the projection pattern of excitation light pattern generating illuminator 42a will be made one-to-one correspondent, both with respect to the pitch and positional relationship, to the imaging pixels as the minimum units of CCD area image sensor 24, this configuration is most preferable in order to make the best use of the resolutions of both components.

Pickup image information from CCD area image sensor 24 is transferred to information processor 41 including a computer etc., by way of a control circuit.

Information processor 41 records numerical information of the 2-dimensional area for surface of detection 44 of a sample, including pickup image information collected by fluorescence image detector 43a, excitation light pattern generating information set up by performing operations based on the pickup image information etc., fluorescence information of the sample, calculated based on the excitation light pattern generating information, the pickup image information corresponding to it and the like, and processes these pieces of information and controls individual connected devices.

The hardware configuration of information processor 41 may be given as a general-purpose computer, a board computer, or an entity that is accessed through a network.

Next, the operation of the fluorescence detecting apparatus according to the second embodiment will be described.

The presumed sample to be the studied by fluorescence detection is a process in which multiple fluorescent spots having significantly great differences in fluorescent intensity gradually vary in their intensity and position over time, as in a case where a sample held in a gel plate or the like becomes fractionated over a 2-dimensional region by 2-dimensional electrophoresis.

To begin with, at the first step, while excitation light pattern generating illuminator 42a irradiates the whole detection area with excitation light of uniform intensity, fluorescence image detector 43a captures the fluorescence image at that time, so that information processor 41 recognizes fluorescence intensity at individual positions. Since this step is aimed at detecting fluorescent spots having intensity higher than a certain level, the intensity of excitation light illumination from excitation light pattern generating illuminator 42a is set at a weak level.

Further, the imaging exposure time of area image sensor 24 by fluorescence image detector 43a may be set at a short period, or the aperture of the imaging lens optical system may be set at a high value.

Next, in the second step, the information processor generates an excitation light pattern generating information such as not to illuminate with excitation light the point and therearound in which a fluorescent spot has been detected at the previous step, and excitation light pattern generating illuminator 42a illuminates with the patterned excitation light.

Since this step is aimed at detecting fluorescent spots that were hard to detect at the previous step because of their low intensity, a fluorescence image is taken by fluorescence image detector 43a while excitation light having a higher intensity than the previous step is being illuminated, and the fluorescence intensity at each position is recognized by information processor 41. Further, the imaging exposure time of area image sensor 24 by fluorescence image detector 43a may be set longer than that in the previous step, or the aperture of the imaging lens optical system may be set at a value lower than that of the previous step.

In fluorescence detecting apparatus of the present embodiment, similarly to the case of the first embodiment it is possible to implement multiple steps similar to the second step, one to another, including the N steps (N=3, 4, . . . ), aiming at executing multiple classes of the second step.

With this arrangement, it becomes possible to realize an operation of a fluorescence detecting apparatus having a high sensitivity over a wide dynamic range, by effectively making use of the features of apparatus components, such as the selectable range of excitation light intensity, the sensitive range of the CCD area image sensor, the selectable range of imaging exposure time, etc.

The excitation light illumination intensity, the imaging exposure time of CCD area image sensor 24 and the like at the first step, as well as the excitation light illumination intensity pattern, the imaging exposure time of CCD area image sensor 24 and the like at and after the second step, may be set up taking into account the characteristics of the fluorescence intensity etc. of the subject to be detected and the optical component configuration of fluorescence image detector 43a and the sensitivity characteristics of CCD area image sensor 24, etc.

Information processor 41 basically calculates the effective fluorescence intensity at every detected point on the surface of detection 44 of the sample, based on the intensity of the irradiated excitation light and the fluorescence intensity detected correspondingly. The fluorescence intensity may be comprehensively calculated from multiple times of detection results under different detecting conditions. Further, when, for example some area at which an extremely high fluorescence is emitted is located adjacent to a detected point, in other words, when the surrounding condition exerts some influence on the detection result of the detected spot, a correction may be made taking into account the degree of that influence.

When, due to variation in the characteristics of a component such as micromirror array device 11 or the like of excitation light pattern generating illuminator 42a, some irregular distribution of the intensity excitation light occurs over the surface of detection 44 of the sample despite that the intensity of the excitation light is set uniform, when some fluctuation that is different from the designated setup occurs on the surface of detection 44 of the sample despite that a predetermined projection pattern is selected, or in any other cases, it is possible to keep the necessary uniformity by correcting the light intensity every projection pixel, which is the minimum unit of the projection pattern of excitation light pattern generating illuminator 42a.

The above correction is preferably made to the excitation light pattern generating information at information processor 41 so as to correct the illumination intensity of the actual excitation light to be irradiated. Alternatively, it is also possible to make correction numerically upon the fluorescence intensity calculation at information processor 41 after actual detection has been made.

When variation due to a component such as CCD area image sensor 24 or the like of fluorescence image detector 43a affects the detection result, it is also possible to make correction numerically upon fluorescence intensity calculation at information processor 41.

When the projection pixels as the minimum units of the projection pattern in excitation light pattern generating illuminator 42a and the imaging pixels as the minimum unit of imaging of CCD area image sensor 24 are made exactly in alignment with each other without any deviation in a one-to-one correspondent manner with respect to their pitch and positional relationship, it is most preferable to make the best use of both the resolutions.

However, it is not so easy to exactly match these conditions especially when devices such as micromirror array device 11, CCD area image sensor 24 etc., are selected from the existing devices to construct the apparatus, taking into account their cost, performances, etc.

The correspondence relationship between the projection pixels of excitation light pattern generating illuminator 42a and the imaging pixels of fluorescence image detector 43a, which is depends on various factors such as a discrepancy caused by the specifications of these devices, discrepancy due to variations etc., in manufacturing the apparatus, discrepancy caused by the apparatus configuration, the shape of the object to be detected and the positional relationship between these, may and should be recorded as previous information in the information processor and used to make correction.

As in the present embodiment, in an optical configuration in which the optical axis of excitation light pattern generating illuminator 42a to the surface of detection 44 of a sample and the optical axis of fluorescence image detector 43a are arranged coaxially on the surface of detection, it is possible to provide a configuration in which the correspondence between the projection pixels of excitation light pattern generating illuminator 42a and the imaging pixels of fluorescence image detector 43a will never change even if the distance from the main lens to the surface of detection 44 is varied.

Accordingly, this configuration is suitable especially when the size of the surface of detection area or the distance to the surface of detection 44 need to be significantly changed on purpose. Yet, it is necessary to consider the occurrence of some loss of light intensity due to additional insertion of optical parts into the light paths for illumination and detection.

Further, the present embodiment has been described referring to an example using micromirror array device 11 as an excitation light pattern means, but the excitation light pattern means may employ a reflection-type liquid crystal device.

As this example, it is possible to configure an excitation light pattern generating illuminator 42 using constituents of an LCD projector using a reflection-type liquid crystal panel LCOS (liquid crystal on silicon). Other basic configuration and operation conform to the first embodiment, hence detailed description is omitted. The device used for the excitation light pattern means may and should be selected taking into consideration the excitation light wavelength range, device specifications, optical characteristics, cost and other factors.

<Description of the Third Embodiment>

Figure 6:
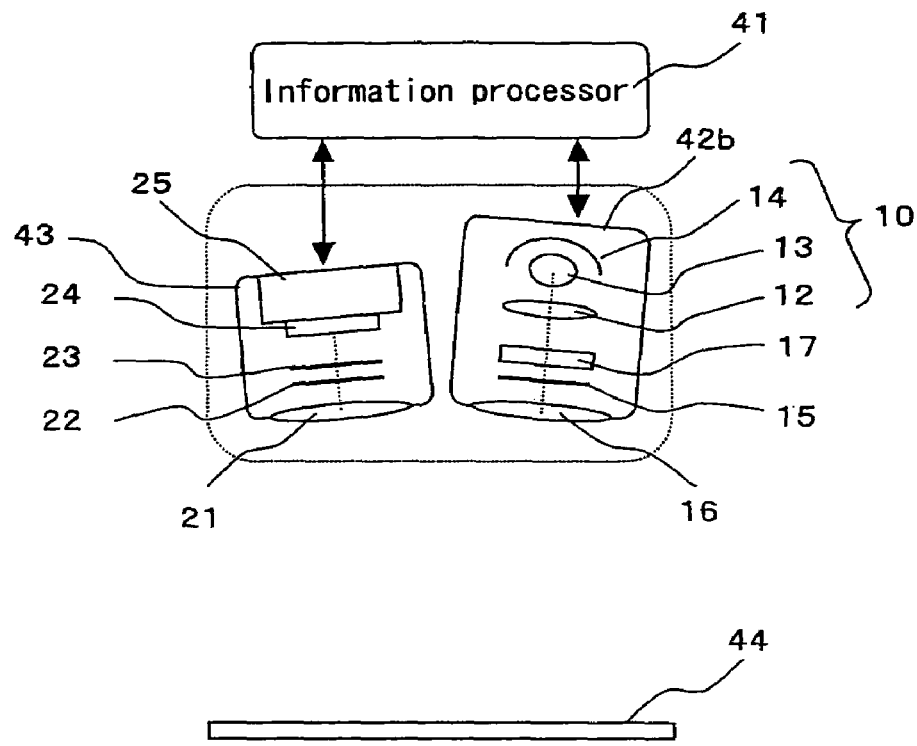
FIG. 6 is a sectional view showing a schematic configuration of a fluorescence detecting apparatus according to the third example embodiment.

FIG. 6 is a schematic configurational view showing a fluorescence detecting apparatus according to the third example embodiment.

The fluorescence detecting apparatus of the third embodiment is comprised of an excitation light pattern generating illuminator 42b, a fluorescence image detector 43 and an information processor 41.

In excitation light pattern generating illuminator 42b, light emitted from a light source 10 passes through a transmission-type liquid crystal device 17 and to be projected to the surface of detection 44 of a sample via a projection lens 16.

Light source 10 is composed of a lamp 13, a light source mirror 14 arranged at the rear of the lamp and a light source lens 12 for irradiating light onto transmission-type liquid crystal device 17. Transmission-type liquid crystal device 17 is controlled by a control circuit in accordance with the excitation light pattern generating information so that the transmittance of light from the light source 10 is controlled for every liquid crystal pixel, to thereby form a 2-dimensional excitation light pattern on the surface of detection 44 of a sample.

When lamp 13 of light source 10 is a white-light source or the like, emitting light over a wide range of wavelengths, an optical filter 15 such as a band-pass filter, color filter, etc., is arranged in the course of the optical path in order to limit the excitation light to be illuminated on the sample to a predetermined wavelength range. Optical filter 15 can be disposed before or behind optical lens 12, or before or behind projection lens 16.

Light source 10 may use a lamp such as a high-pressure mercury lamp, metal halide lamp, xenon lamp or the like, or may use a high-brightness LED, high-brightness fluorescent tube etc. Further, the configurations and shapes of light source mirror 14 and light source lens 12 or whether they should be used or not can be made choice of, considering the characteristics of light source devices such as luminescence anisotropy etc. The constituents of a liquid crystal projector system using a transmission-type liquid crystal device may be used to constitute an excitation light pattern generating illuminator 42b.

Since fluorescence image detector 43 and information processor 41 as well as the operation etc., of the fluorescence detecting apparatus substantially conforms to the fluorescence detecting apparatus of the aforementioned first embodiment, detailed description is omitted.

<Description of the Fourth Embodiment>

The fluorescence detecting apparatus of this embodiment (not shown) is comprised of an excitation light pattern generating illuminator and a fluorescence image detector, which are arranged so as to partly share a coaxial optical system, and an information processor, and the excitation light pattern generating illuminator is composed of a transmission-type liquid crystal device. That is, this embodiment is a configuration that employs part of the above second and third embodiments in combination. Since the fluorescence image detector and information processor as well as the operation etc., of the fluorescence detecting apparatus substantially conforms to the fluorescence detecting apparatus of the aforementioned second embodiment, detailed description is omitted.

Other than above, any device as long as it includes a mechanism capable of projecting motion pictures, such as CRT projectors etc., can be used as an excitation light pattern generating illuminator. Hence it is possible to select one as a constituent of the excitation light pattern generating illuminator, taking into consideration the excitation light wavelength range, device specifications, optical characteristics, cost and other factors.

<Description of the Fifth Embodiment>

Figure 7:
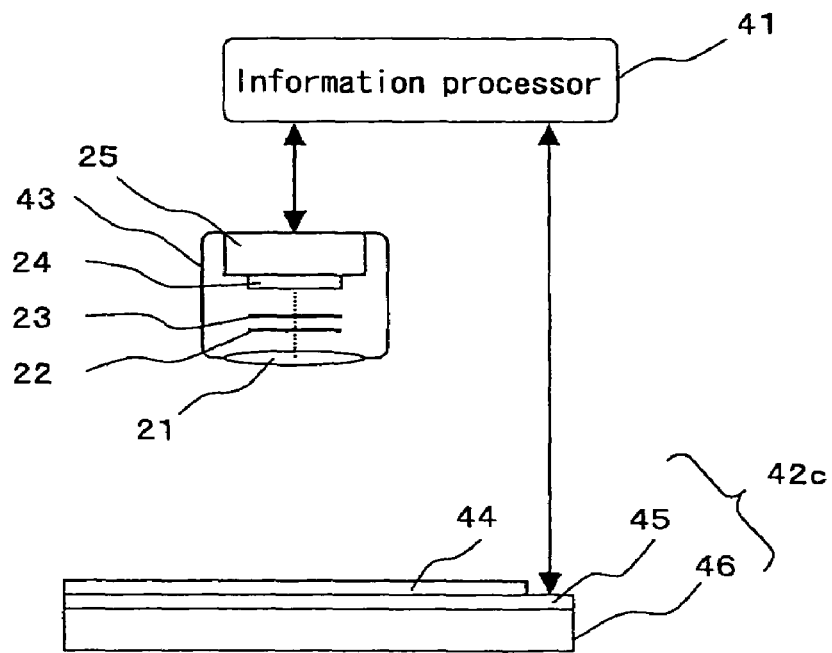
FIG. 7 is a sectional view showing a schematic configuration of a fluorescence detecting apparatus according to the fifth example embodiment.

FIG. 7 is a schematic configuration of a fluorescence detecting apparatus according to the fifth example embodiment.

The fluorescence detecting apparatus of this embodiment is comprised of an excitation light pattern generating illuminator 42c, a fluorescence image detector 43 and an information processor 41, and excitation light pattern generating illuminator 42c is arranged on the rear side of the fluorescence image surface of detection 44.

Excitation light pattern generating illuminator 42c includes a liquid crystal panel 45 arranged on a backlight 46. With this arrangement, the surface of detection 44 of a sample is illuminated with excitation light from the rear side. It is possible to arrange an optical filter etc., for limiting the excitation light wavelengths, on the top of or underside transmission-type liquid crystal panel 45. It is also possible to arrange a micromirror array etc., taking into account the use efficiency of light and the illumination area of the sample surface.

Since fluorescence image detector 43 and information processor 41 as well as the operation etc., of the fluorescence detecting apparatus basically conforms to the fluorescence detecting apparatus of the above embodiment, detailed description is omitted.

This embodiment shows an example of using a flat-type light-emitting display device for excitation light pattern generating illuminator 42c, and is configured by a combination of backlight 46 and liquid crystal panel 45. However, the present invention should not be limited to this as long as the desired wavelengths, light intensity, number of pixels and the like can be obtained. For example, organic EL (electro luminescence) panels, inorganic EL panels, LED displays, PDPs (plasma display panels), CRTs (cathode ray tubes) and others can be applied.

What is claimed is:

1. A fluorescence detecting apparatus comprising:
    a light source device for illuminating a sample with excitation light;
    a fluorescence detecting device for detecting fluorescence emitted from the sample; and
    an excitation light pattern generating device for generating an illumination pattern of excitation light to be irradiated over the surface under observation of the sample, in accordance with the detected result from fluorescence detecting device.

2. The fluorescence detecting apparatus according to claim 1, wherein the excitation light pattern generating device comprises a micromirror array device.

3. The fluorescence detecting apparatus according to claim 1, wherein the excitation light pattern generating device comprises a reflection-type liquid crystal device.

4. The fluorescence detecting apparatus according to claim 1, wherein the excitation light pattern generating device comprises a transmission-type liquid crystal device.

5. The fluorescence detecting apparatus according to claim 1, wherein the fluorescence detecting device comprises a CCD area image sensor.

6. The fluorescence detecting apparatus according to claim 5, wherein the fluorescence detecting device comprises an electronic cooling device.

7. The fluorescence detecting apparatus according to claim 6, wherein the excitation light pattern generating device is arranged so that the minimum unit area of the excitation light pattern generating device which receives excitation light irradiated from the light source device and generates a pattern of the excitation light and the unit detection area of the fluorescence detecting device are approximately equal in size and position to each other on the sample surface from which fluorescence is emitted.

8. The fluorescence detecting apparatus according to claim 5, wherein the excitation light pattern generating device is arranged so that the minimum unit area of the excitation light pattern generating device which receives excitation light irradiated from the light source device and generates a pattern of the excitation light and the unit detection area of the fluorescence detecting device are approximately equal in size and position to each other on the sample surface from which fluorescence is emitted.

9. The fluorescence detecting apparatus according to claim 1, wherein the excitation light pattern generating device is arranged so that the minimum unit area of the excitation light pattern generating device which receives excitation light irradiated from the light source device and generates a pattern of the excitation light and the unit detection area of the fluorescence detecting device are approximately equal in size and position to each other on the sample surface from which fluorescence is emitted.

* * * * *